United States Patent
Nishimura et al.

(10) Patent No.: US 8,920,420 B2
(45) Date of Patent: Dec. 30, 2014

(54) SCISSORS FOR ENDOSCOPE

(75) Inventors: Miyuki Nishimura, Nagano (JP);
Makoto Nishimura, Nagano (JP)

(73) Assignee: Kaneka Corporation, Osaka (JP)

( * ) Notice: Subject to any disclaimer, the term of this patent is extended or adjusted under 35 U.S.C. 154(b) by 407 days.

(21) Appl. No.: 13/500,707

(22) PCT Filed: Oct. 5, 2010

(86) PCT No.: PCT/JP2010/067453
§ 371 (c)(1),
(2), (4) Date: Apr. 6, 2012

(87) PCT Pub. No.: WO2011/043340
PCT Pub. Date: Apr. 14, 2011

(65) Prior Publication Data
US 2012/0197253 A1  Aug. 2, 2012

(30) Foreign Application Priority Data

Oct. 8, 2009   (JP) .................. 2009-234668

(51) Int. Cl.
| | | |
|---|---|---|
| A61B 18/18 | (2006.01) | |
| A61B 17/3201 | (2006.01) | |
| A61B 17/29 | (2006.01) | |
| A61B 17/32 | (2006.01) | |
| A61B 10/06 | (2006.01) | |
| A61B 19/00 | (2006.01) | |
| A61B 18/14 | (2006.01) | |

(52) U.S. Cl.
CPC ............. *A61B 17/3201* (2013.01); *A61B 17/29* (2013.01); *A61B 17/320016* (2013.01); *A61B 10/06* (2013.01); *A61B 2019/305* (2013.01); *A61B 2018/146* (2013.01)
USPC .......................................... 606/46

(58) Field of Classification Search
CPC .................. A61B 10/06; A61B 17/29; A61B 17/320016; A61B 17/3201; A61B 2018/146; A61B 2019/305; A61B 18/149; A61B 18/1485; A61B 2018/1861
USPC ........................................... 606/46
See application file for complete search history.

(56) References Cited

U.S. PATENT DOCUMENTS

| | | | |
|---|---|---|---|
| 7,935,130 B2 * | 5/2011 | Williams | ...................... 606/208 |
| 2003/0208201 A1 | 11/2003 | Iida et al. | |
| 2005/0075631 A1 | 4/2005 | Kidooka | |

FOREIGN PATENT DOCUMENTS

| | | |
|---|---|---|
| CN | 2862977 Y | 1/2007 |
| DE | 10316132 A | 4/2003 |

(Continued)

*Primary Examiner* — George Manuel
(74) *Attorney, Agent, or Firm* — Bacon & Thomas, PLLC

(57) ABSTRACT

Scissors (1) for an endoscope includes a treatment section (5) provided with a pair of scissor elements (10, 11) which are pivotably supported by a pivoting shaft (support pin (13)) and are pivotally displaced between an open position and a closed position; an operation wire (3) connected to the treatment section (5), and an operation section for displacing the scissor elements (10, 11) between the open position and the closed position by advancing and retracting the operation wire (3). A stopper (14) is provided to the treatment section (5). In the open position, the stopper (14) restricts the relative movement between the pair of scissor elements (10, 11) in the opening direction, and in the closed position, the stopper (14) restricts the relative movement between the pair of scissor elements (10, 11) in the closing direction, thereby to restrict excessive opening and closure of the scissor elements.

14 Claims, 6 Drawing Sheets

(56) References Cited

FOREIGN PATENT DOCUMENTS

| | | | |
|---|---|---|---|
| EP | 1568330 | A1 | 8/2005 |
| JP | 6296619 | A | 10/1994 |
| JP | 10179602 | A | 7/1998 |
| JP | 2003299669 | A | 10/2003 |
| JP | 2005204998 | A | 8/2005 |
| JP | 2009090060 | A | 4/2009 |

* cited by examiner

SCISSORS FOR ENDOSCOPE

BACKGROUND OF THE INVENTION

1. Field of the Invention

The present invention relates to scissors for an endoscope passed within a treatment device guide channel of the endoscope to be movable forward and backward and intended for use to incise or resect a body tissue such as adhesion, mucosal tissue or the like in a body cavity.

2. Description of the Conventional Art

There are well-known treatment devices each passed within a treatment device guide channel of an endoscope to incise or resect a body tissue such as adhesion, mucosal tissue or the like in the body cavity. As one example of such conventional treatment devices, scissors for an endoscope is disclosed in the patent document 1 cited herein.

The scissors for an endoscope disclosed in the patent document 1 includes an operation section provided at the rear or base end of the treatment device, an insert section connected to the operation section, and a treatment section provided at the front end of the insert section and having a pair of scissor elements which can be opened and closed. Of the scissors, the scissor elements are opened and closed by pushing and pulling an operation wire passed inside the insert section by manipulating the operation section. The scissor elements are opened and closed directly by a linkage mechanism provided between the scissor elements and operation wire. To incise or resect an adhesion or the like in the body cavity, the scissor elements are opened, applied to the adhesion and then closed.

PRIOR ART DOCUMENTS

Patent Document

Patent Document 1:
Japanese Published Unexamined Application No. 204998 of 2005

SUMMARY OF THE INVENTION

Problem to be Solved by the Invention

However, the conventional scissors for an endoscope is not designed to restrict the angle of opening of scissor elements. Therefore, it is likely that the front ends of elements 100a and 100b of the scissors will be excessively opened or spaced from each other as shown in FIG. 10. Also the scissor elements 100a and 100b will be possibly closed so excessively that they intersect each other and their front ends protrude outward as shown in FIG. 11. Such excessive opening or outward protrusion of the front ends of scissor elements will possibly result in contact of the front ends of the scissor elements with any other portion than a body tissue going to be resected or result in something undesirable like that.

Further, if an operation wire 101 is pulled excessively (the scissor elements 100a and 100b are closed excessively) as shown in FIG. 11, a linkage member 102a included in a linkage mechanism 102 will be longitudinally parallel to the operation wire 101, that is, a support pin 102b, pivot pin 102c and sliding pin 102d included in the linkage mechanism 102 will be in alignment with the operation wire 101. In such a case, a large force will be required to push in the operation wire 101 for opening the scissor elements 100a and 100b or it will be impossible to push in the operation wire 101, which will possibly lead to damage to the scissors.

Also, to avoid the above, the operator of such a surgical endoscope has to make fine adjustment of the angle of opening of the scissor elements 100a and 100b by adjusting the force for advancing or retracting the operation wire when he or she opens or closes the scissor elements 100a and 110b, which is rather difficult for the operator to cope well with.

To overcome the above-mentioned drawbacks of the prior art, it is an object of the present invention to provide highly safe scissors for an endoscope configured in such a manner that the angle of opening of the scissor elements can be restricted and that excessive opening and closure of the scissor elements can be suppressed.

According to a first aspect of the present invention, there is provided scissors for an endoscope including a treatment section including a pair of scissor elements which are pivotably supported by a pivoting shaft and are pivotally displaced between an open position and a closed position, an operation wire connected to the treatment section, and an operation section for displacing the scissor elements between the open position and the closed position by advancing and retracting the operation wire, Wherein a stopper is provided at the treatment section, which restricts the relative movement between the pair of scissor elements in the opening direction when the scissor elements are in the open position, while restricting the relative movement between the pair of scissor elements in the closing direction when the scissor elements are in the closed position.

According to a second aspect of the present invention, there is provided scissors for an endoscope configured in such a manner that when the scissor elements are in the closed position, the operation wire being advanced or retracted applies a load component about the pivoting shaft to the scissor elements in the first aspect of the present invention.

According to a third aspect of the present invention, there is provided scissors for an endoscope, wherein the stopper is provided on at least one of the pair of scissor elements in such a manner that when the scissor elements are in the closed position, it abuts with a blade formed on the inner side of the other scissor element anteriorly to the pivoting shaft and that when the scissor elements are in the open position, it abuts an arm of the other scissor element which extends to rearward of the pivoting shaft in the first and second aspects of the invention.

According to a fourth aspect of the present invention, there is provided scissors for an endoscope, wherein the stopper is formed as a rectangular parallelepiped of which the first side face being one longitudinal side face abuts the inside edge of the rearward extending arm when the scissor elements are in the open position and the second side face adjacent to the first side face abuts the blade when the scissor elements are in the closed position in the third aspect of the invention.

According to a fifth aspect of the present invention, there is provided scissors for an endoscope, wherein the stopper is provided on each of the pair of scissor elements in the first and second aspects of the invention.

According to a sixth aspect of the present invention, there is provided scissors for an endoscope, wherein the stopper is provided on each of the pair of scissor elements in the first and second aspects of the invention.

According to a seventh aspect of the present invention, there is provided scissors for an endoscope, wherein the stopper is provided on each of the pair of scissor elements in the fourth aspect of the invention.

According to an eighth aspect of the present invention, there is provided scissors for an endoscope, wherein the treatment section also includes a linkage mechanism provided between the operation wire and scissor elements to pivotally displace each of the scissor elements in pair, and the stopper is provided at the linkage mechanism in the first or second aspect of the invention.

According to an ninth aspect of the present invention, there is provided scissors for an endoscope, wherein the blade of each of the pair of scissor elements is electrically conductive while almost entire surface of the treatment section including the stopper but not the blades is nonconductive, and a connecting terminal is provided for connecting a high frequency power to the blades in the first or second aspect of the invention.

According to a tenth aspect of the present invention, there is provided scissors for an endoscope, wherein the blade of each of the pair of scissor elements is electrically conductive while almost entire surface of the treatment section including the stopper but not the blades is nonconductive, and a connecting terminal is provided for connecting a high frequency power to the blades in the third aspect of the invention.

According to an eleventh aspect of the present invention, there is provided scissors for an endoscope, wherein the blade of each of the pair of scissor elements is electrically conductive while almost entire surface of the treatment section including the stopper but not the blades is nonconductive, and a connecting terminal is provided for connecting a high frequency power to the blades in the fourth aspect of the invention.

According to a twelfth aspect of the present invention, there is provided scissors for an endoscope, wherein the blade of each of the pair of scissor elements is electrically conductive while almost entire surface of the treatment section including the stopper but not the blades is nonconductive, and a connecting terminal is provided for connecting a high frequency power to the blades in the fifth aspect of the invention.

According to a thirteenth aspect of the present invention, there is provided scissors for an endoscope, wherein the blade of each of the pair of scissor elements is electrically conductive while almost entire surface of the treatment section including the stopper but not the blades is nonconductive, and a connecting terminal is provided for connecting a high frequency power to the blades in the sixth aspect of the invention.

According to a fourteenth aspect of the present invention, there is provided scissors for an endoscope, wherein the blade of each of the pair of scissor elements is electrically conductive while almost entire surface of the treatment section including the stopper but not the blades is nonconductive, and a connecting terminal is provided for connecting a high frequency power to the blades in the seventh aspect of the invention.

According to a fifteenth aspect of the present invention, there is provided scissors for an endoscope, wherein the blade of each of the pair of scissor elements is electrically conductive while almost entire surface of the treatment section including the stopper but not the blades is nonconductive, and a connecting terminal is provided for connecting a high frequency power to the blades in the eighth aspect of the invention.

According to a sixteenth aspect of the present invention, there is provided scissors for an endoscope, wherein the blade of each of the pair of scissor elements is electrically conductive while almost entire surface of the treatment section including the stopper but not the blades is nonconductive, and a connecting terminal is provided for connecting a high frequency power to the blades in the ninth aspect of the invention.

According to a seventeenth aspect of the present invention, there is provided scissors for an endoscope, wherein the blade of each of the pair of scissor elements is electrically conductive while almost entire surface of the treatment section including the stopper but not the blades is nonconductive, and a connecting terminal is provided for connecting a high frequency power to the blades in the tenth aspect of the invention.

According to a eighteenth aspect of the present invention, there is provided scissors for an endoscope, wherein the blade of each of the pair of scissor elements is electrically conductive while almost entire surface of the treatment section including the stopper but not the blades is nonconductive, and a connecting terminal is provided for connecting a high frequency power to the blades in the eleventh aspect of the invention.

Effect of the Invention

As will be known from the foregoing description, the stopper provided in the scissors for an endoscope according to the present invention permits to restrict the angle of opening of the scissor elements to a predetermined one when the scissor elements are opened or closed by manipulating the operation section. Therefore, when the scissor elements are opened, their front ends will not be opened or spaced from each other excessively. On the other hand, when the scissor elements are closed, they will not intersect each other and their front ends will not protrude outward. Thus, the blades of the scissor elements will not possibly be put into contact with any other portion than a body tissue going to be resected.

DESCRIPTION OF EMBODIMENTS

Figure 1:
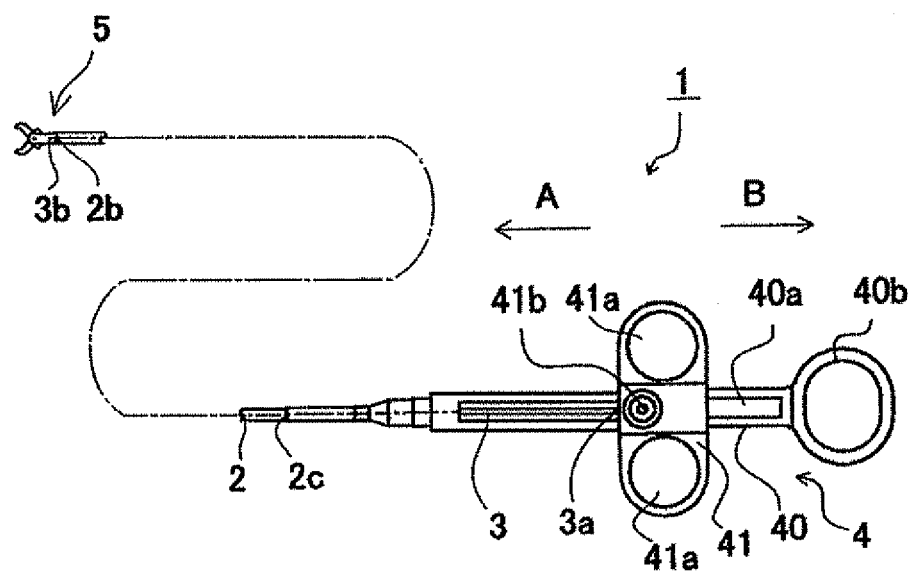
FIG. 1 is an external overall view of the scissors for an endoscope as one embodiment of the present invention
Figure 2:
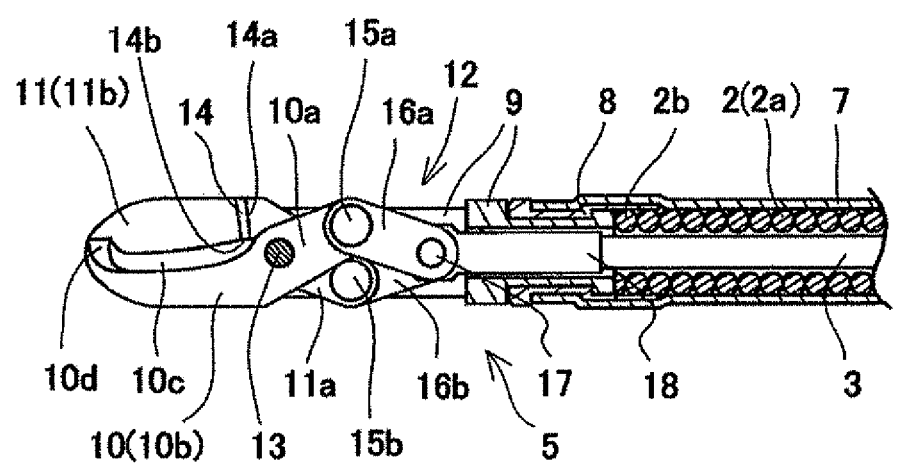
FIG. 2 is an enlarged fragmentary sectional view of the treatment section in which the scissor elements are in the closed position
Figure 3:
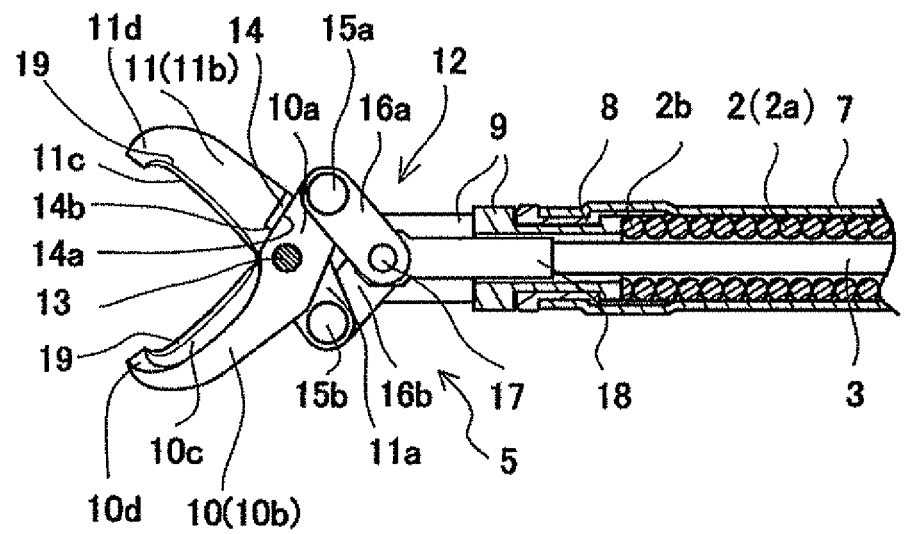
FIG. 3 is an enlarged fragmentary sectional view of the treatment section in which the scissor elements are in the open position
Figure 4:
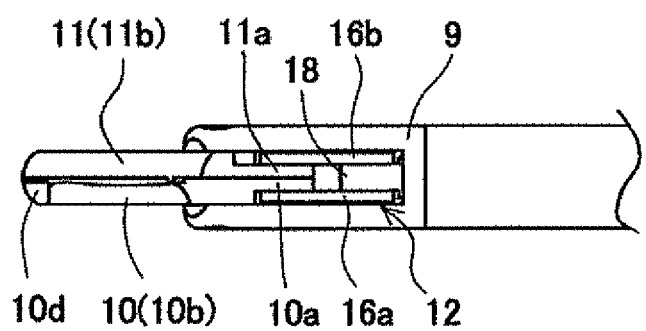
FIG. 4 is an enlarged plan view of the treatment section.
Figure 5:
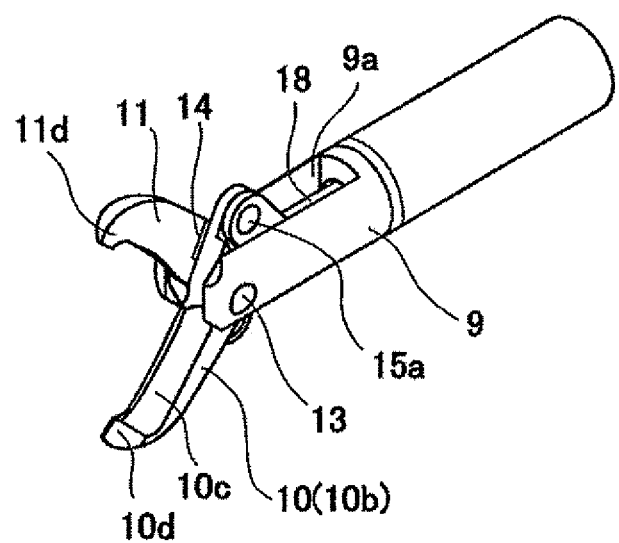
FIG. 5 is an enlarged perspective view of the treatment section.

The present invention according to the present invention will be described in detail hereunder concerning the embodiment of the scissors for an endoscope and its variants with reference to the accompanying drawings FIG. 1 is an overall view of one embodiment of the scissors for an endoscope (will be referred to as "endoscope scissors" hereunder) according to the present invention. The FIGS. 2 and 3 are enlarged fragmentary sectional views showing the treatment section with the scissor elements being in the closed position and in the open position, respectively. FIG. 4 is an enlarged plan view of the treatment section. FIG. 5 is an enlarged perspective view of the treatment section.

First there will be outlined the one embodiment of the endoscope scissors according to the present invention, generally indicated with a reference numeral 1.

As shown, the endoscope scissors 1 includes a treatment section 5 including a pair of scissor elements 10 and 11 which are pivotably supported by a pivoting pin (support pin 13) and pivotally displaced between an open position and a closed position, an operation wire 3 connected to the treatment section 5, and an operation section 4 for displacing the scissor elements 10 and 11 between the open position and the closed position by advancing and retracting the operation wire 3. The endoscope scissors 1 has also provided at the treatment section 5 thereof a stopper 14 which restricts the relative movement between the pair of scissor elements 10 and 11 in the opening direction when the scissor elements 10 and 11 are in the open position, while restricting the relative movement between the pair of scissor elements (10, 11) in the closing direction when the scissor elements 10 and 11 are in the closed position.

The endoscope scissors 1 according to this embodiment will be described in further detail below.

The endoscope scissors 1 includes a flexible sheath 2, operation wire 3 passed within the sheath 2, operation section 4 provided at a rear or base end 2c of the sheath 2, and the treatment section 5 connected to a front end 2b of the sheath 2 and front end 3b of the operation wire 3.

The sheath 2 is a flexible coil pipe 2a formed from a metallic wire such as a stainless steel wire coiled in close contact between adjacent turns. Also, the outer surface of the coil pipe 2a is covered with a sheath cover 7 along the entire length thereof. The sheath cover 7 is a nonconductive flexible tube. The sheath 2 is laid in a treatment device guide channel (not illustrated) of the endoscope.

The sheath cover 7 is fixed with bondage, adhesion or the like to the outer circumference of a front-end ferrule 8 fixedly fitted on the front end 2b of the coil pipe 2a.

The sheath 2 has the operation wire 3 loosely passed within it. The operation wire 3 is a single wire or a twisted wire. The operation wire 3 can be axially advanced and retracted and also rotated on an axis by manipulating the operation section 4 connected to the rear or base end 2c of the sheath 2 shown in FIG. 1.

It should be noted that the sheath 2 may be made of only a flexible tube of PTFE (polytetrafluoroethylene), PEEK (polyether ether ketone), polyethylene, polyimide resin or the like in lieu of the coil pipe 2a in this embodiment.

The operation section 4 includes a main body 40 and a slider 41 slidably fitted on the main body 40 and to which a rear or base end 3a of the operation wire 3 is connected.

The main body 40 of the operation section 4 has a recess 40a formed therein along a predetermined length. The slider 41 is fitted in the recess 40a to be slidable axially (rightward in the plane of FIG. 1).

Also a finger handle 40b is provided at the rear end of the main body 40 and a pair of right and left finger handles 41a (upper and lower finger handles in the plane of FIG. 1) is provided on the slider 41. Further, the slider 41 has fixed thereto a connecting terminal 41b to which a high frequency power cord is to be connected. With the connecting terminal 41b connected to a high frequency power source (not illustrated), a high frequency current can be supplied to the treatment section 5 through the operation wire 3.

The operator advances or retracts the operation wire 3 axially in the sheath 2 by sliding the slider 41 axially relative to the main body 40 of the operation section 4 with the thumb being applied to the finger handle 40b and forefinger and middle finger applied to the finger handles 41a, respectively. FIG. 1 shows the treatment section 5 of which the scissor elements 10 and 11 are opened by pushing the slider 41 (finger handles 41a) away from the finger handle 40b (in the direction indicated with an arrow A in FIG. 1). On the contrary, the scissor elements 10 and 11 of the treatment section 5 can be closed by moving the slider 41 toward the finger handle 40b (in the direction indicated with an arrow B in FIG. 1). It should be noted that opening and closing the scissor elements 10 and 11 of the treatment section 5 by moving the slider 41 as above will be described in detail later.

The treatment section 5 includes a front-end support frame 9 fitted to the front-end ferrule 8 rotatably on an axis. The front-end ferrule 9 has a slit 9a formed therein as shown in FIG. 5. As shown in FIGS. 4 and 5, the first and second scissor elements 10 and 11 and a linkage mechanism 12 are supported in the slit 9a. The first and second scissor elements 10 and 11 in pair, linkage mechanism 12 and front-end support frame 9 form together the treatment section 5.

The front-end support frame 9 is formed from stainless steel, ceramics or high heat resistance plastic (PEEK, PPS (polyphenylene sulfide resin) or the like). At the front end of the front-end support frame 9, there is provided the support pin 13 as a pivot pin as shown in FIG. 5. The first and second scissor elements 10 and 11 are pivotably supported on this support pin 13 with their nearly middle portions being placed together to face each other. The linkage mechanism 12 is connected to these scissor elements 10 and 11 in such a manner that manipulating the main body 40 of the operation section 4 and slider 41 permits to open and close the scissor elements 10 and 11.

The first and second scissor elements 10 and 11 are formed each like a thin sickle. The portions of the first and second scissor elements 10 and 11 extending rearward from the portions of the scissor elements 10 and 11 pivotably supported on the support pin 13 will be referred to as "rearward extending arms 10a and 11a", respectively, hereunder. The ends of the rearward extending arms 10a and 11a are connected by pivot pins 15a and 15b to the linkage mechanism 12. That is, the pivot pins 15a and 15b will apply a load to the scissor elements 10 and 11. As the pivot pins 15a and 15b are pulled toward the rear or base end by the operation wire 3, the scissor elements 10 and 11 are pivoted about the support pin 13 and thus their free ends are displaced toward each other so that the treatment section 5 takes the closed position. On the contrary, when the pivot pins 15a and 15b are pushed toward the front end by the operation wire 3, the scissor elements 10 and 11 are pivoted about the support pin 13 and thus their free ends are turned away from each other so that the treatment section 5 takes the open position.

The portions of the first and second scissor elements 10 and 11 extending anteriorly to the support pin 13 are scissor portions 10b and 11b curved inwardly relative to each other. The scissor portions 10b and 11b will nip, resect or cauterize a body tissue.

As shown, each of the scissor portions 10b and 11b has two sides, at one (will be referred to as "inner side" hereunder) of which the scissor portions 10b and 11b overlap each other and on the other (will be referred to as "outer side" hereunder) of which each scissor portion 10b (11b) has formed on one edge thereof a sharp blade 10c (11c) raked toward the edge. The scissor portion 10b (11 b) has no blade formed on an edge (back) opposite to the raked edge (blade 10c (11c)) but is formed arcuate near the front end.

Also, the blades 10c and 11c have formed at the front ends thereof protrusions 10d and 11d extending inwardly, respectively. The protrusions 10d and 11d have no blade formed thereon.

At the treatment section 5 there is provided the stopper 14 to prevent the front ends of the scissor elements 10 and 11 once set in the open position from being further opened while preventing the front ends of the scissor elements 10 and 11 once set in the closed position from being further closed.

In this embodiment, the stopper 14 is provided on each of the scissor elements 10 and 11 of the treatment section 5. However, it should be noted that the stopper 14 may be provided at the linkage mechanism 12 including links 16a and 16b and the pivot pins 15a and 15b (see FIGS. 8 and 9).

Also, this embodiment will be explained concerning an aspect that one stopper 14 is used in common to restrict the pivotal displacement of the scissor elements 10 and 11 between the open and closed positions. It should be noted however that there may be provided individually in different places a first stopper to prevent the scissor elements 10 and 11 in the open position from being further opened and a second stopper to prevent the scissor elements 10 and 11 in the closed position from being further closed. In other words, a plurality of stoppers 14 may be provided in a plurality of places.

As shown in FIGS. 2 and 3, the stopper 14 in this embodiment is provided on at least one (scissor element 11 as shown) of the pair of scissor elements 10 and 11. When the treatment section 5 is in the closed position, the stopper 14 abuts a more frontward portion of the blade 10c of the other scissor element 10 than the pivoting shaft (support pin 13) as shown in FIG. 2. On the other hand, when the treatment section 5 is in the open position, the stopper 14 abuts the other scissor element 10 at the arm 10a extending to rearward of the pivoting shaft (support pin 13) as shown in FIG. 3. Thus, the maximum angle of opening between the first and second scissor elements 10 and 11 is restricted.

The stopper 14 is provided on each of the scissor elements 10 and 11 in pair. More specifically, the stopper 14 is provided on the inner side of the scissor portion 11b of the scissor element 11 and another stopper is provided on the inner side of the scissor portion 10b of the scissor element 10, which is not illustrated. The latter stopper will abut the blade 11c of the second scissor element 11 when the first and second scissor elements 10 and 11 are closed, while it will abut the rearward extending arm 11a of the second scissor element 11 when the first and second scissor elements 10 and 11 are opened.

The stopper 14 is formed as a rectangular parallelepiped of which the first side face 14a being one longitudinal side face abuts the inside edge of the rearward extending arm 10a when the scissor elements 10 and 11 are in the open position as shown in FIG. 3. The second side face 14b adjacent to the first side face 14a abuts the blade 10c when the scissor elements 10 and 11 are in the closed position as shown in FIG. 2. More particularly, the first side face 14a includes, as at least a portion thereof, a ridge extending along the inside edge of the rearward extending arm 10a. That is, when the first side face 14a abuts the inside edge, a part or whole of the ridge will abut the inside edge. Also, the second side face 14b includes, as at least a portion thereof, a ridge extending along the blade 10c. That is, when the second side face 14b abuts the blade 10c, a part or whole of the ridge will abut the blade 10c.

The stopper 14 provided as above restricts the angle of opening between the first and second scissor elements 10 and 11 so that the scissor elements 10 and 11 are opened and closed to the positions where they abut the stopper 14 and within the restricted angle of opening.

In this embodiment, the stopper 14 provided at the treatment section 5, not at the operation section 4 or operation wire 3, assures a high reproducibility of opening and closure of the scissor elements 10 and 11. For example, in case a stopper to restrict the movement of the slider 41 is provided at the operation section 4, it is difficult for the stopper to attain perfect suppression of excessive opening and closure of the scissor elements 10 and 11. The reason for this is as follows. With the sheath 2 being inserted in the treatment device guide channel of an endoscope introduced in a curved body cavity, the path inside the curved channel will be different in length from that outside the curved channel and hence a relative displacement will occur between the support pin 13 fixed at the front end of the sheath 2 and the operation wire 3 inside the sheath 2. Thus, even if the operation wire 3 is fixed to the operation section 4, the support pin 13 will be displaced relative to the operation wire 3, which will lead to pivoting of the scissor elements 10 and 11. In other words, even if the operation wire 3 is fixed at the rear or base end thereof, it is not possible to optimally restrict the angle of opening between the scissor elements 10 and 11 of the treatment section 5. In the endoscope scissors 1 according to this embodiment, however, the stopper 14 provided at the treatment section 5 permits to restrict the angle opening of the scissor elements 10 and 11 as desired independently of how the sheath 2 is bent or curved. Especially in case the stopper 14 is provided at each of the scissor elements 10 and 11 as in this embodiment, the linkage mechanism 12 of the treatment section 5 will not possibly be damaged and thus high stability of opening and closure of the treatment section 5 can be maintained even with repetition of the opening and closing operations.

Also the stoppers 14 each formed as a rectangular parallelepiped as in this embodiment can be put into plane contact with the scissor elements 10 and 11 respectively. Thus, the pressure applied to the stoppers 14 when the scissor elements 10 and 11 are restricted from being pivoted can be dispersed, and so the stoppers 14 will not possibly damage the blades 10c and 11c of the scissor elements 10 and 11.

In the foregoing, the present invention has been described concerning the example in which the stopper 14 is provided on each of the scissor portions 10b and 11b. However, it should be noted here that the stopper 14 may be provided at either of the scissor portions 10b and 11b.

Also, by providing a stopper 14 at each of the pair of scissor elements 10 and 11, it is possible to disperse the pressure applied to the stoppers 14, which permits to provide endoscope scissors 1 being not subject to breakage but highly safe.

The blades 10c and 11c of the pair of scissor elements 10 and 11 are electrically conductive. Almost entire surface of the treatment section 5 including the stopper 14 but not the blades 10c and 11c is nonconductive. The endoscope scissors 1 has a connecting terminal 41b for applying a high frequency power to the blades 10c and 11c.

More particularly, there is provided a linear live part 19 on the edge of each of the blades 10c and 11c as shown in FIG. 3. The scissor elements 10 and 11 are applied with a coordinate-phase high frequency voltage through the operation wire 3 made of a conductive material such as copper, coupling member 18 and links 16a and 16b. At this time, the scissor elements 10 and 11 serve each as a monopolar high-frequency electrode and can thus cauterize a body tissue between them linearly.

Each of the scissor elements 10 and 11 has provided on the surface thereof except for the live part 19 a nonconductive coating of a fluorine resin or the like. Making almost entire surface of the treatment section 5 nonconductive in this manner permits to prevent a body tissue to be cauterized from adhering to the treatment section 5. Since the surface of the stopper 14 is also nonconductive, any cauterized body tissue will not adhere to the stopper 14. Therefore, the scissor elements 10 and 11 in the open and closed positions will not incur any position variation. In other words, since no cauterized body tissue adheres to the stopper 14, the function of the latter will not be adversely affected.

Figure 6:
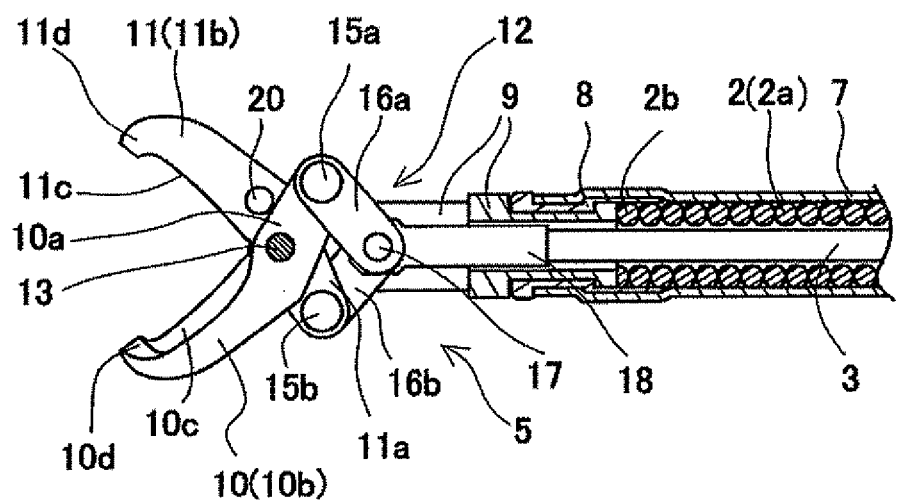
FIG. 6 is an enlarged fragmentary sectional view of the treatment section in a first variant of the embodiment in FIG. 1 in which the stopper is modified.

In the embodiment having been described in the foregoing, the stopper 14 is formed as a parallelepiped by way of example. However, the present invention is not limited to this example but the stopper may be formed cylindrical (stopper 20) as in the first variant of this embodiment shown in FIG. 6, for example. Further, by changing the installed position, size and the like of the stopper 14, the angle of opening between the scissor elements 10 and 11 can be set as desired. Also, the stoppers 14 and 20 may be provided to be positionally variable relative to the scissor elements 10 and 11 so that varying the positions of the stoppers 14 and 20 permits to increment or decrement the maximum angle of opening between the scissor elements 10 and 11 in the open positions. More specifically, the installed positions of the stoppers 14 and 20 may be selected according to an intended manner in which the endoscope scissors 1 is to be used. For example, a recess or the like may be formed in each of the scissor portions 10b and 11b so that the stoppers 14 and 20 can be slid longitudinally of the scissor portions 10c and 10c and fixed in desired positions, respectively, or a similar arrangement may be made.

The linkage mechanism 12 connected to the scissor elements 10 and 11 includes the rearward extending arms 10a and 11a forming a part of the scissor elements 10 and 11, respectively, links 16a and 16b, support pin 13, pivot pin 15a and 15b and a slide pin 17.

The link 16a is connected at one end thereof pivotally, by the pivot pin 15a, to the rear or base end of the rearward extending arm 10a included in the scissor element 10. The link 16b is connected at one end thereof pivotally, by the pivot pin 15b, to the rear or base end of the rearward extending arm 11a included in the scissor element 11. The slide pin 17 is connected pivotally to the other ends of these links 16a and 16b. Furthermore, the slide pin 17 has connected thereto the coupling member 18 fixed to the front end of the operation wire 3. The coupling member 18 supports the slide pin 17 and is slidably engaged on the front-end support frame 9.

As the coupling member 18 forming a part of the linkage mechanism 12 is slid along the front-end support frame 9, the slide pin 17 provided on the coupling member 18 slides forward and rearward along with the coupling member 18. That is, the end portions of the links 16a and 16b will move along with the forward and rearward movement of the slide pin 17. On the other hand, since the support pin 13 is fixed at the front end of the front-end support frame 9, the slide pin 17 will move toward and away from the support pin 13, that is, the distance between them will decrease and increase.

Thus, the angle defined between the rearward extending arm 10a and link 16a, joined to each other by the pivot pin 15a, these elements being included in the first scissor element 10, and that defined between the rearward extending arm 11a and link 16b, joined to each other by the pivot pin 15b, these elements being included in the second scissor element 11, increase or decrease together. That is, the first and second scissor elements 10 and 11 can be opened away from each other as shown in FIG. 3 or they can be closed to overlap each other as shown in FIG. 2.

The endoscope scissors 1 constructed as having been described above is operated by the operator with the thumb being applied to the finger handle 40b and forefinger and middle finger being applied to the finger handles 41a. By sliding the slider 41 axially in relation to the main body 40 of the operation section 4, the slider 41 is moved forward away from the finger handle 40b (in the direction indicated with the arrow A in FIG. 1). As the slider 41 is thus moved forward, the operation wire 3 connected to the slider 41 is advanced inside the sheath 2. As the operation wire 3 is thus moved forward, the coupling member 18 connected to the front end 3b of the operation wire 3 moves along the front-end support frame 9, the distance of the slide pin 17 to the support pin 13 is increased and thus the first and second scissor elements 10 and 11 are opened. On the contrary, sliding the slider 41 toward the finger handle 40b (in the direction indicated with the arrow B in FIG. 1) permits to close the first and second scissor elements 10 and 11.

When advanced or retreated axially with the first and second scissor elements 10 and 11 of the treatment section 5 being in the closed position as shown in FIG. 2, the operation wire 3 will apply a load component about the pivoting shaft (support pin 13) to the scissor elements 10 and 11. More particularly, when the scissor elements 10 and 11 are in the closed position, the direction, in which the points (pivot pins 15a and 15b) at which the load component is applied to the scissor elements 10 and 11 are connected to the pivoting shaft (support pin 13), intersects that in which the operation wire 3 is advanced or retracted. Thus, while the treatment section 5 is in the closed position, the linkage mechanism 12 will not fall on a dead point. In other words, while the links 16a and 16b are not overlapping each other, the second side face 14b of the stopper 14 abuts the scissor portion 10b of the scissor element 10. Therefore, just advancing the operation wire 3 toward its front end permits to switch the scissor elements 10 and 11 from the closed position shown in FIG. 2 to the open position shown in FIG. 3.

A body tissue is to be resected with the endoscope scissors 1 by opening the scissor elements 10 and 11 through manipulation of the main body 40 of the operation section 4 and the slider 41, positioning the body tissue between the scissor elements 10 and 11, and then closing the scissor elements 10 and 11 through manipulation of the main body 40 of the operation section 4 and the slider 41.

In this variant, the edge portions of the scissor elements 10 and 11 opposite to the respective blades 10c and 11c of the scissor portions 10b and 11b are formed arcuate near the front end. This assures a high safety of the treatment section 5. For example, when the treatment section 5 is projected from the treatment device guide channel of the endoscope into the body cavity, it will not possibly injure any other body tissue than a body tissue going to be resected even if it is put into contact with the other body tissue.

Also, the blades 10c and 11c have inward extending protrusions 10d and 11d at the front ends thereof, respectively. Since these protrusions 10d and 11d serve to hold a body tissue going to be resected, it is possible to prevent the body tissue from being pushed out forward and leaving the treatment section 5.

The live parts 19 are formed like a curved line along the blades 10c and 11c of the scissor elements 10 and 11 up to the protrusions 11d and 11d. Thus, a body tissue can be cauterized with the scissor elements 10 and 11 by pushing the body tissue forward with the blades 10c and 11c, holding it with the protrusions 10d and 11d and enclosing it full circumferentially between the live parts 19.

Figure 7:
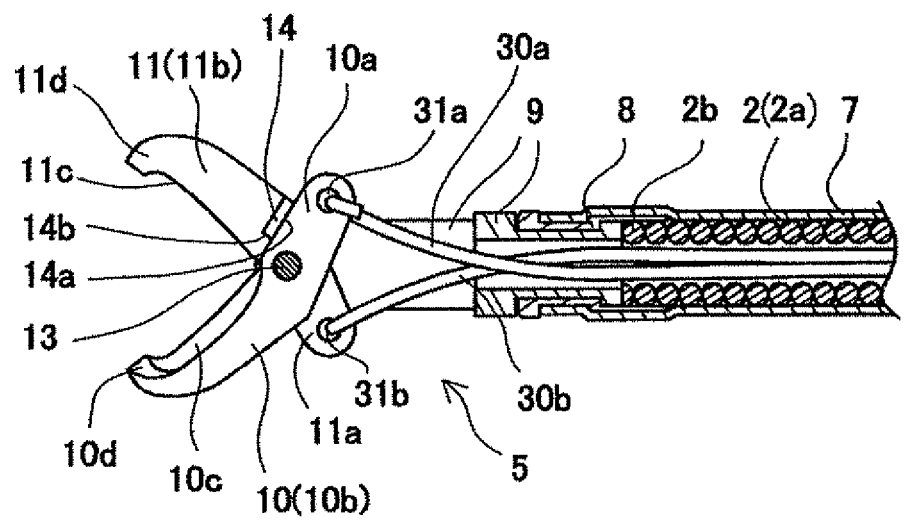
FIG. 7 is an enlarged fragmentary sectional view of the treatment section in a second variant of the embodiment in FIG. 1 in which no linkage mechanism is used.

In this first variant, the linkage mechanism 12 is used to open and close the treatment section 5. However, it should be noted that the present invention is not limited to this variant. For example, holes 31a and 31b may be formed in the first and second scissor elements 10 and 11, respectively and operation wires 30a and 30b may be secured to these holes 31a and 31b, respectively, as in the second variant shown in FIG. 7.

Figure 8:
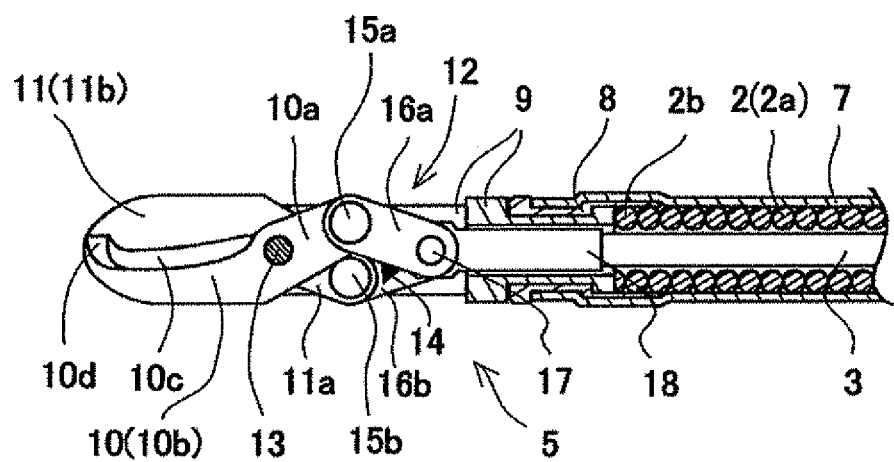
FIG. 8 is an enlarged fragmentary sectional view showing the closed scissor elements in the treatment section in a third variant of the embodiment in FIG. 1 in which the stopper is provided at the linkage mechanism.
Figure 9:
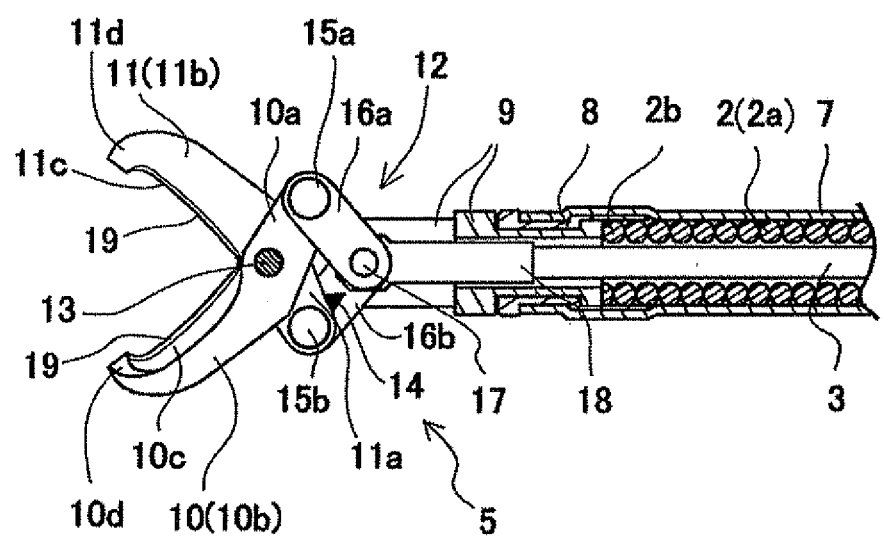
FIG. 9 is an enlarged fragmentary sectional view showing the opened scissor elements in the treatment section in the third variant.
Figure 10:
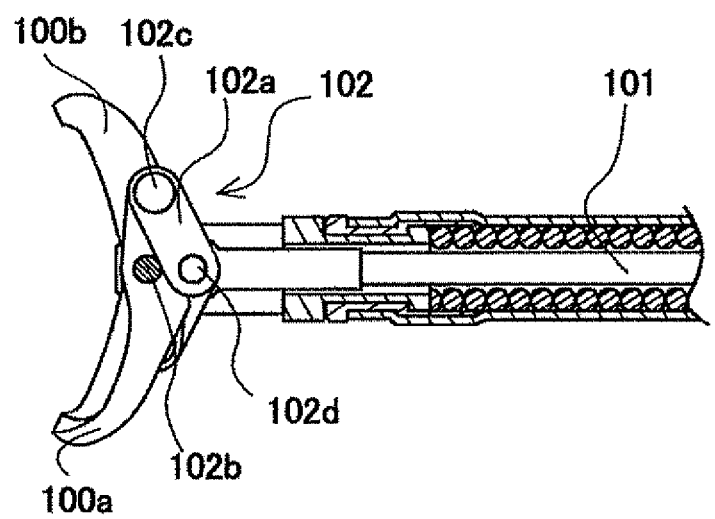
FIG. 10 is an enlarged fragmentary sectional view of the treatment section in the conventional scissors for an endoscope.
Figure 11:
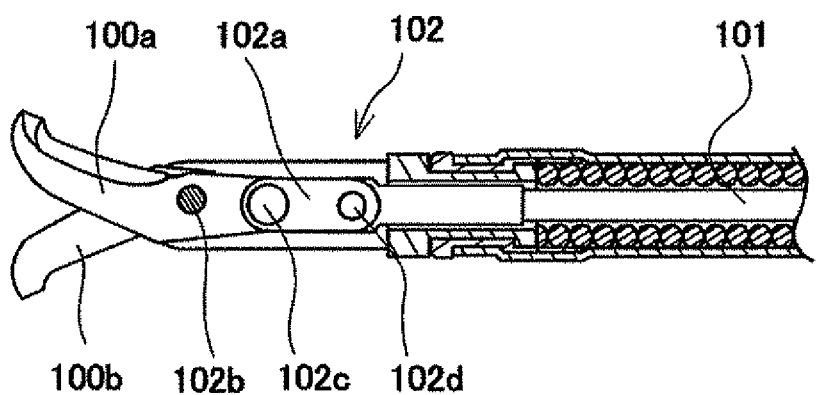
FIG. 11 is an enlarged fragmentary sectional view of the treatment section in the conventional scissors for an endoscope.

FIG. 8 is an enlarged fragmentary sectional view showing the closed scissor elements in the treatment section 5 in the third variant in which the stopper 14 is provided at the linkage mechanism 12. FIG. 9 is an enlarged fragmentary sectional view showing the opened scissor elements in the treatment section 5 in the third variant.

The treatment section 5 further includes a linkage mechanism 12 provided between the operation wire 3 and the scissor elements 10 and 11 to move the pair of scissor elements 10 and 11 pivotally as the operation wire 3 is advanced and retracted. In the endoscope scissors 1 according to the third variant, the stopper 14 is provided at the linkage mechanism 12. More specifically, the stopper 14 is provided at the link 16b.

In this variant, when the treatment section 5 is in the closed position as shown in FIG. 8, the stopper 14 abuts the link 16a from below as shown. When the treatment section 5 is in the open position as shown in FIG. 9, the stopper 14 abuts the rearward extending arm 11a of the scissor element 11 from the right as shown. In this third variant, the stopper 14 is a triangular projection provided on the link 16b to restrict the movement of the linkage mechanism 12 at one of its different sides which is selected depending upon whether the treatment section 5 is in the closed position or in the open position.

As mentioned above, the stopper 14 provided at the treatment section 5 may be provided on either the scissor elements 10 and 11 or the linkage mechanism 12. In case the stopper 14 is provided on the linkage mechanism 12, it may be provided on its link 16a or 16b, support pin 13, pivot pin 15a or 15b, or on its slide pin 17. More particularly, each of these pins may be formed to have a noncircular cross-sectional shape and the holes formed in the scissor elements 10 and 11 and links 16a and 16b to receive the respective pins may also be formed noncircular, to thereby restrict pivotal turn of the pins when the scissor elements 10 and 11 are in either the open position or the closed position.

In the foregoing, the present invention has been described in detail concerning certain preferred embodiment and variants thereof as examples with reference to the accompanying drawings. However, it should be understood by those ordinarily skilled in the art that the present invention is not limited to the embodiment and variants but can be modified in various manners, constructed alternatively or embodied in various other forms without departing from the scope and spirit thereof as set forth and defined in the appended claims.

DESCRIPTION OF REFERENCE NUMERALS

1 . . . Endoscope scissors
2 . . . Sheath
2b . . . Front end
2c . . . Rear or base end
3 . . . Operation wire
3a . . . Rear or base end
3b . . . Front end
4 . . . Operation section
5 . . . Treatment section
10 . . . First scissor element
10a . . . Rearward extending arm
11 . . . Second scissor element
11a Rearward extending arm
11c . . . Blade
13 . . . Support pin
14 . . . Stopper
14a . . . First side face
14b . . . Second side face

What is claimed is:

1. Scissors for an endoscope, comprising:
a treatment section including a pair of scissor elements which are pivotably supported by a pivoting shaft and are pivotally displaced between an open position and a closed position;
an operation wire connected to the treatment section; and
an operation section for displacing the scissor elements between the open position and the closed position by advancing and retracting the operation wire,
wherein a stopper is provided at the treatment section, which restricts the relative movement between the pair of scissor elements in the opening direction when the scissor elements are in the open position, while restricting the relative movement between the pair of scissor elements in the closing direction when the scissor elements are in the closed position; and
wherein the stopper is provided on at least one of the pair of scissor elements in such a manner that when the scissor elements are in the closed position, the stopper abuts a blade formed on the inner side of the other scissor element anteriorly to the pivoting shaft and that when the scissor elements are in the open position, the stopper abuts an arm of the other scissor element which extends to rearward of the pivoting shaft.

2. The scissors of claim 1, wherein when the scissor elements are in the closed position, the operation wire being advanced or retracted applies a load component about the pivoting shaft to the scissor elements.

3. The scissors of claim 2, wherein the stopper is formed as a rectangular parallelepiped of which the first side face being one longitudinal side face abuts the inside edge of the rearward extending arm when the scissor elements are in the open position and the second side face adjacent to the first side face abuts the blade when the scissor elements are in the closed position.

4. The scissors of claim 3, wherein the stopper is provided on each of the pair of scissor elements.

5. The scissors of claim 2, wherein the stopper is provided on each of the pair of scissor elements.

6. The scissors of claim 1, wherein the stopper is formed as a rectangular parallelepiped of which the first side face being one longitudinal side face abuts the inside edge of the rearward extending arm when the scissor elements are in the open position and the second side face adjacent to the first side face abuts the blade when the scissor elements are in the closed position.

7. The scissors of claim 6, wherein the stopper is provided on each of the pair of scissor elements.

8. The scissors of claim 6, wherein the blade of each of the pair of scissor elements is electrically conductive while almost entire surface of the treatment section including the stopper but not the blades is nonconductive, and a connecting terminal is provided for connecting a high frequency power to the blades.

9. The scissors of claim 1, wherein the stopper is provided on each of the pair of scissor elements.

10. The scissors of claim 1, wherein the blade of each of the pair of scissor elements is electrically conductive while almost entire surface of the treatment section including the stopper but not the blades is nonconductive, and a connecting terminal is provided for connecting a high frequency power to the blades.

11. Scissors for an endoscope, comprising:
a treatment section including a pair of scissor elements which are pivotably supported by a pivoting shaft and are pivotally displaced between an open position and a closed position;
an operation wire connected to the treatment section; and
an operation section for displacing the scissor elements between the open position and the closed position by advancing and retracting the operation wire,
wherein a stopper is provided at the treatment section, which restricts the relative movement between the pair of scissor elements in the opening direction when the scissor elements are in the open position, while restricting the relative movement between the pair of scissor elements in the closing direction when the scissor elements are in the closed position; and
wherein the blade of each of the pair of scissor elements is electrically conductive while almost entire surface of the treatment section including the stopper but not the blades is nonconductive, and a connecting terminal is provided for connecting a high frequency power to the blades.

12. The scissors of claim 11, wherein when the scissor elements are in the closed position, the operation wire being advanced or retracted applies a load component about the pivoting shaft to the scissor elements.

13. The scissors of claim 11, wherein the stopper is provided on each of the pair of scissor elements.

14. The scissors of claim 11, wherein the treatment section includes a linkage mechanism provided between the operation wire and scissor elements to pivotally displace each of the scissor elements in pair, and the stopper is provided at the linkage mechanism.

* * * * *

UNITED STATES PATENT AND TRADEMARK OFFICE
CERTIFICATE OF CORRECTION

PATENT NO.        : 8,920,420 B2
APPLICATION NO.   : 13/500707
DATED             : December 30, 2014
INVENTOR(S)       : Miyuki Nishimura et al.

It is certified that error appears in the above-identified patent and that said Letters Patent is hereby corrected as shown below:

On the Title Page:

"(73)  Assignee:   Kaneka Corporation, Osaka (JP)"

should read:

--(73)  Assignee:   River Seiko Corporation, Okaya-shi, Nagano (JP);
                    Kaneka Corporation, Osaka (JP)--

Signed and Sealed this
Fifteenth Day of December, 2015

Michelle K. Lee
*Director of the United States Patent and Trademark Office*